(12) United States Patent
Barr

(10) Patent No.: US 7,966,096 B2
(45) Date of Patent: Jun. 21, 2011

(54) SYSTEMS AND METHODS FOR ISOBUTYL ALCOHOL (IBA) RECOVERY

(75) Inventor: Russell Barr, Millis, MA (US)

(73) Assignee: Invensys Systems, Inc., Foxboro, MA (US)

( * ) Notice: Subject to any disclaimer, the term of this patent is extended or adjusted under 35 U.S.C. 154(b) by 1931 days.

(21) Appl. No.: 10/199,832

(22) Filed: Jul. 19, 2002

(65) Prior Publication Data

US 2003/0018590 A1 Jan. 23, 2003

Related U.S. Application Data

(60) Provisional application No. 60/306,542, filed on Jul. 19, 2001.

(51) Int. Cl.
*G05B 21/00* (2006.01)

(52) U.S. Cl. ........ 700/266; 700/268; 700/271; 700/273; 436/43; 436/52; 436/139; 422/61; 422/67; 422/68.1

(58) Field of Classification Search .................... 73/1.01, 73/1.02; 422/50, 61, 62, 63, 67, 68.1, 81, 422/82; 436/43, 52, 139; 700/266, 268, 700/273, 271; 201/1, 28, 30; 202/81, 82, 202/164; 203/1, 3, 18, 71
See application file for complete search history.

(56) References Cited

U.S. PATENT DOCUMENTS

| | | | | |
|---|---|---|---|---|
| 3,602,701 A | * | 8/1971 | Boyd, Jr. .......................... 700/36 |
| 4,295,037 A | | 10/1981 | Miller | |
| 4,642,167 A | * | 2/1987 | Berg et al. ......................... 203/60 |
| 4,724,049 A | * | 2/1988 | Berg et al. ......................... 203/51 |
| 5,134,574 A | | 7/1992 | Beaverstock et al. | |
| 5,217,579 A | * | 6/1993 | Kusakabe et al. .............. 202/154 |
| 5,449,440 A | * | 9/1995 | Rescalli et al. .................. 203/20 |
| 5,483,007 A | * | 1/1996 | Johnson ......................... 525/403 |
| 5,559,275 A | * | 9/1996 | Barger ........................... 568/905 |
| 5,703,133 A | * | 12/1997 | Vanderspurt et al. .......... 518/707 |
| 5,795,447 A | * | 8/1998 | Berg ................................ 203/57 |
| 5,811,602 A | * | 9/1998 | Vanderspurt et al. ...... 568/902.2 |
| 6,034,141 A | * | 3/2000 | Vanderspurt et al. .......... 518/713 |

FOREIGN PATENT DOCUMENTS

EP 0 530 432 A 10/1993
EP 0 718 266 A 6/1995

* cited by examiner

Primary Examiner — Brian J Sines
(74) Attorney, Agent, or Firm — Foley Hoag LLP (57) ABSTRACT

Methods and systems for creating dynamic performance measures (DPMs) for an IBA manufacturing process. Included is a method for monitoring an Isobutyl Alcohol (IBA) recovery system that includes computing at least one of an amount of IBA recovered from the IBA recovery system and an amount of waste material produced from the IBA recovery system, and displaying at least one of the recovered IBA and the waste material produced based on time. The method also includes computing a cost saved based on a cost of virgin IBA and the amount of IBA recovered. Computing an amount of waste material includes measuring waste material flow, and computing a cost of waste material management based on the measured waste material flow and a cost per unit volume to dispose of waste material. The IBA recovery system can include an evaporation IBA recovery system and/or a distillation IBA recovery system.

10 Claims, 5 Drawing Sheets

SYSTEMS AND METHODS FOR ISOBUTYL ALCOHOL (IBA) RECOVERY

CLAIM OF PRIORITY

This application claims priority to U.S. Ser. No. 60/306,542, entitled "Dynamic Performance Measures For IBA Manufacturing Processes," filed on Jul. 19, 2001, naming Russell Barr as inventor, the contents of which are herein incorporated by reference in their entirety.

BACKGROUND (1) Field

The disclosed methods and systems relate generally to process control indicators, and more particularly to real-time indicators for improved performance process control in a manufacturing process that includes Isobutyl Alcohol (IBA).

(2) Description of Relevant Art

In a process plant, various processes are employed to produce amounts of a desired product. Traditional methods to measure general performance of manufacturing operations of a certain product include counting the amount of product produced over a certain period of time, and from that amount, calculating a cost per unit product. The cost per unit product is typically based on a standard cost function that is associated with the operation, often developed at the beginning of a fiscal time period, and utilized throughout that period. The cost per unit product is also often reported to manufacturing management to evaluate manufacturing performance, and often serves as a primary measure of manufacturing performance.

One disadvantage of measuring manufacturing performance by cost per unit product is the equal distribution and allocation of plant costs to each product or product line in the determination of cost per unit product, or alternately and additionally, cost allocation based on an algorithm that does not assign costs correctly. Often, costs in a manufacturing plant are not directly assignable to a product or product line, and therefore costs must be allocated based on other factors that usually have more to do with the perceived performance of the manufacturing operation than the actually occurring manufacturing practices.

Another disadvantage of measuring manufacturing performance by cost per unit product is that a considerable percentage of the costs in a manufacturing plant for calculating the cost per unit product, are not within the scope of manufacturing's authority; therefore, the performance measurement of cost per unit product leads to a "volume base" manufacturing approach that may not properly satisfy market and corporate requirements.

Furthermore, determining cost per unit product can be based on the amount of each product or product line produced, and this calculation may not be sensitive to problems incurred in the producing a specific product. For example, if a bad batch of a given product is produced and discarded, a standard allocation algorithm may not assign the costs associated with that batch to the specific product, and the costs are allocated to all products.

Other approaches to measuring manufacturing performance involve non-cost/non-financial measurements and include measurements of quality, delivery integrity, and customer satisfaction. These approaches are generally directed to the discrete manufacturing industry and involve collecting information and displaying results in a traditional daily, weekly, or monthly report format. Such approaches do not provide timely measurements to allow operations personnel to improve the process on which the measurements were made.

In manufacturing processes wherein Isobutyl Alcohol (IBA) is used, the cost of procuring and disposing of IBA waste can be a significant cost factor in the production of a product. One industry that utilizes IBA is the pharmaceutical industry. In a competitive market such as pharmaceutical manufacturing, competition can be extreme, especially in those commodity markets where pharmaceuticals are off-patent and can hence be manufactured by an FDA-approved manufacturer. These generic drug manufacturers can operate with a downward price pressure on their products and a critical need to control costs to achieve a reasonable profit margin.

SUMMARY

The disclosed methods and systems include a method for monitoring an Isobutyl Alcohol (IBA) recovery system that includes computing at least one of an amount of IBA recovered from the IBA recovery system and an amount of waste material produced from the IBA recovery system, and, displaying at least one of the recovered IBA and the waste material produced based on time. The method also includes computing a cost saved based on a cost of virgin IBA and the amount of IBA recovered. The amount of waste material can be computed by measuring waste material flow and computing a cost of waste material management based on the measured waste material flow and a cost per unit volume to dispose of waste material. The method can also include measuring at least one of a flow rate of recovered IBA and a flow rate of waste material.

The disclosed methods and systems can be employed with an IBA recovery system that includes an evaporation IBA recovery system, a distillation IBA recovery system, or a combination thereof.

Computing an amount of IBA recovered from the IBA recovery system can include determining an amount of BA recovered per unit volume and determining a market cost of IBA per unit volume. The computing can also include providing a measurement of recovered IBA to a processor module coupled to receive the measurement, and, processing the measurement to indicate the amount of IBA recovered. The methods and systems can also include providing an alarm when the computed value of IBA recovered satisfies at least one criterion, and/or an alarm when the computed value of waste material produced satisfies at least one criterion.

Computing an amount of waste material produced from the IBA recovery system can include providing a measurement of waste material to a signal processing module coupled to receive the measurement, and processing the measurement to indicate the amount of waste material produced.

Some embodiments that utilize evaporation recovery units, for example, can include measuring a cost of steam provided to the IBA recovery system, and computing a steam cost per unit of IBA recovered based on the flow rate of recovered IBA and the measured cost of steam. These embodiments can also measure a flow of steam to the IBA recovery system, and compute a measure of IBA recovery system steam cost based on the flow of steam and a cost of steam generation. Additionally and optionally, in some embodiments, the methods and systems can measure electrical consumption related to the IBA recovery system, and compute a measure of IBA recovery system electricity cost based on the measured electrical consumption and a cost of electricity.

The systems and methods also include a system for monitoring an Isobutyl Alcohol (IBA) manufacturing process that includes an IBA recovery system including at least one of an IBA recovery container and a waste container, at least one sensor to provide measurements related to at least one of the IBA recovery container contents and the waste container contents, a processor to process the at least one sensor data and compute at least one of a value representing a volume of the IBA recovery container contents and a value representing a volume of the waste container contents, and, a display to display data based on at least one of the value representing the volume of the IBA recovery container contents and the value representing the volume of the waste container contents. The at least one sensor includes a flow meter, and/or the processor can compute at least one of a volume of IBA recovered per unit time and an amount of waste per unit time. The processor can compute at least one of a cost of IBA recovered per unit time and a cost of waste management per unit time. The display can display or otherwise represent at least one of a volume of IBA recovered per unit time, an amount of waste per unit time, a cost of IBA recovered per unit time, a cost of waste management per unit time, and a throughput.

Also disclosed is a control system for a process having an Isobutyl Alcohol (IBA) recovery system, where the control system includes at least one sensor to provide signals related to at least one of an amount of IBA recovered from the IBA recovery system and an amount of waste produced by the IBA recovery system, a processor to receive and process the signals to compute at least one value related to the amount of IBA recovered and the amount of waste produced, and, a display to display data based on at least one of the value related to the amount of IBA recovered and the value related to the amount of waste produced. The control system can include a control algorithm related to the IBA recovery system and based on the at least one measurement related to the amount of IBA recovered and the amount of waste produced. The at least one sensor includes a flow meter.

The methods and systems include a method for controlling a process having an Isobutyl Alcohol (IBA) recovery system that includes providing measurements related to at least one of an amount of IBA recovered from the IBA recovery system and an amount of waste produced by the IBA recovery system, processing the measurements to compute at least one value representing the amount of IBA recovered and the amount of waste produced, and, displaying data based on at least one of the value representing the amount of IBA recovered and the value representing the amount of waste produced. The processing includes computing at least one dynamic performance measure based on at least one of the value representing the amount of IBA recovered and the cost of virgin IBA, and the amount of waste produced and the cost of waste disposal. The displayed data includes graphically presenting at least one dynamic performance measure based on at least one of the value representing the amount of IBA recovered and the cost of virgin IBA, and the amount of waste produced and the cost of waste disposal. Also provided can be at least one alarm threshold related to at least one of an amount of IBA recovered and an amount of waste produced, and the at least one alarm can be displayed.

The systems and methods include a Dynamic Performance Measure (DPM) for an Isobutyl Alcohol (IBA) recovery system, the DPM including a display having at least one of an amount of IBA recovered from the IBA recovery system and an amount of waste material produced from the IBA recovery system. The DPM includes a means for providing a cost of virgin IBA, a means for providing a measure of waste material flow and a means for providing cost per unit volume to dispose of waste material, and/or a means for providing at least one of a flow rate of recovered IBA and a flow rate of waste material.

Other objects and advantages will become obvious hereinafter in the specification and drawings.

DESCRIPTION

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the disclosed systems or methods.

For the described methods and systems, a processor can be understood to be a processor-controlled device that can include, for example, a PC, workstation, handheld, palm, laptop, cellular telephone, or other processor-controlled device that includes instructions for causing the processor to act in accordance with the disclosed methods and systems. References to "a processor" or "the processor" can be understood to include one or more processors that can communicate in a stand-alone and/or a distributed environment(s), and can thus can be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application.

The disclosed methods and systems include dynamic performance measures (DPMs) for an Isobutyl Alcohol (IBA) manufacturing process. In an embodiment, IBA recovery and waste material production can be optimized by aggregating sensor measurements from sensors that produce outputs indicating the amounts of IBA recovered and waste material generated, respectively. The respective sensor measurements can be processed to form a measurement that can be utilized to determine measures in the form of DPMs that relate to the productivity and cost of the IBA recovery and waste management processes. The DPMs can be provided to a display that can be viewed by manufacturing or other personnel. Control decisions can be made to change the IBA recovery and/or waste production processes while the results of such changes can be reflected in real-time on the DPM displays.

The disclosed systems and methods thus include a real-time (dynamic), sensor-based performance measurement and control. The measurement and control can operate within a manufacturing or process plant having multiple processes that form an output product. The processes can be operated in a pattern to provide manufacturing operations. The control apparatus can employ multiple sensors coupled to the processes and at least one processor for providing a real-time indication of manufacturing operation performance from sensor signals. Performance can be indicated in terms of quality of generated products, cost of production, down-time, yield, and/or production.

Figure 1:
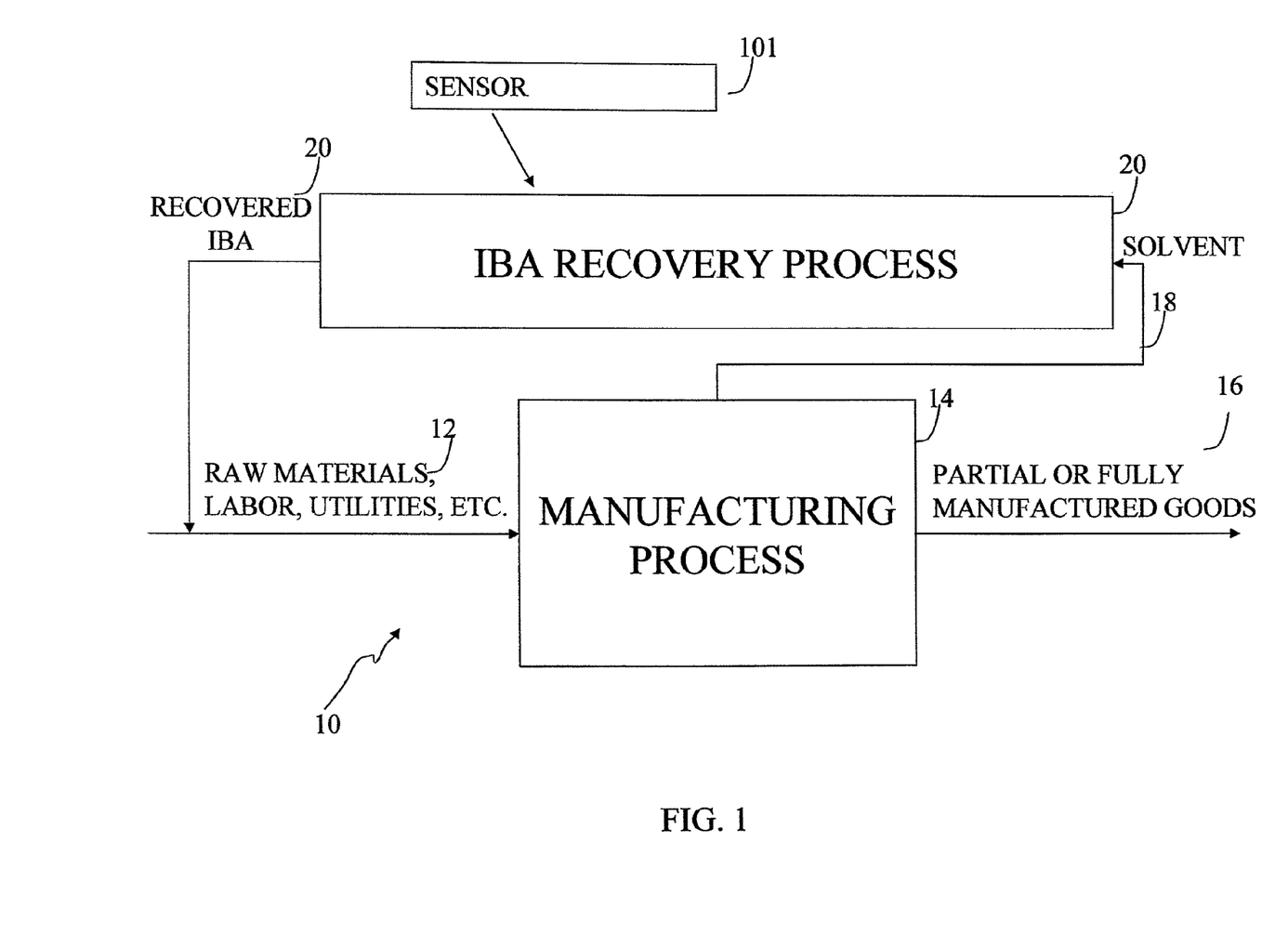
FIG. 1 illustrates one Isobutyl Alcohol (IBA) manufacturing process.

Sensors, including but not limited to representative sensor 101 shown in FIG. 1, can provide signals indicative of a current, present, or existing state of a respective IBA recovery process. A digital processor, for example, can be coupled to the sensors to receive the sensor signals. One or more processors equipped with a display can support the digital processor to determine, from the sensor signals, a quantitative measurement of present performance of the IBA recovery process based on present operation of the IBA recovery process. For example, the processor(s) can compute or otherwise calculate production cost based on sensed present amounts of resources used, and calculate quantity of production based on sensed rate of operation of the IBA recovery process. Accordingly, the display can generally provide a graphical or other representation of economic performance, including for example, a graph, plot, bar graph, pie chart, or other representation.

The processor can further display data that can indicate present performance of the IBA recovery process relative to or based on a predetermined target performance measurement. A control apparatus coupled to the process can allow operator adjustment to cause states of the IBA recovery process to approach operation that provides a predetermined target performance of the manufacturing operations.

The processor(s) or computer can also provide audible and/or visible alarms based on determined performance measurements. The alarms can be coupled to the digital processor or another processor. For example, the processor can provide an alarm when certain criteria are satisfied by the IBA recovery process and/or by a determined performance. In one example, the processor can enable an alarm when a determined performance measurement based on present cost of production exceeds a predefined threshold, and/or when determined performance measurement based on quality is outside a predefined range.

Accordingly, a measure of present performance of a manufacturing or plant operation, or process unit(s) of a plant or manufacturing operation, can be computed based on sensor measurements. Process units can include, for example, pumps, storage vessels, transfer lines, valves, etc., found in a processing or manufacturing plant. Also, sensors can include temperature sensors, weight sensors, pressure sensors, etc.

In one embodiment, the digital processor can include processor modules, and different sensors can be coupled to the different processor modules. Processor modules can have an object manager to transmit respective sensor signals to a processor or computer upon request by the processor. Sensor signals can be formed using named series of data points stored in a memory area, and object managers can enable access of data points by name instead of memory location.

The processor can be coupled to an external system for receiving pertinent predefined measurements of target performance. A control apparatus can be coupled to the digital processor. Additionally, a processor member supported by the digital processor can receive working data from the computer and store the working data on a common time-line in a global database for general access. The working data can include determined performance measurements, predetermined target measurements, indications of sensed states of process means, operator adjustments, and predefined thresholds for alarms. The database can be a relational database accessible globally at subsequent times as desired for different applications.

In one embodiment, the disclosed IBA recovery methods and system can be applied to the production and/or manufacture of pharmaceutical products. The pharmaceutical products can be, for example, Vancomycin. In a pharmaceutical manufacturing or production system, sensors can provide measurements that can be related to the recovery and/or disposal of IBA. In an embodiment, performance measures can be formed to indicate the amount of IBA waste, and relate that waste to waste management costs. Sensors including, for example, flow meters or other measurement devices can provide input to the performance measures to allow engineering, manufacturing, production, etc., personnel to reduce manufacturing costs as a function of IBA recovery.

Those of ordinary skill in the art will recognize that other manufacturing processes, including the fertilizer industry, adhesive industry, and other industries, can employ IBA and hence IBA recovery systems and processes. Accordingly, the disclosed methods and systems can be applied to these and other industries without departing from the scope of the disclosure. Further, the methods and systems can be used in IBA recovery systems that utilize distillation techniques, evaporation techniques, or combinations thereof.

FIG. 1 shows an illustrative block diagram 10 of a manufacturing process that uses Isobutyl Alcohol (IBA) to manufacture goods or products. Several major manufacturing industries, including the pharmaceutical manufacturing industry, utilize IBA in the manufacturing process, although those with ordinary skill in the art will recognize that the methods and systems herein are not limited to the FIG. 1 system or the pharmaceutical industry.

By-products of a manufacturing process utilizing IBA can be classified as hazardous waste and accordingly can require incineration at either an on-site or off-site facility. Although incineration is costly, off-site incineration can be more expensive than on-site treatment. By recovering IBA from the by-products, the amount of hazardous waste can be reduced. Additionally, IBA recovery can reduce manufacturing costs by reducing the need for additional, virgin IBA to be introduced to the manufacturing process. The combination of reduced necessity for new or virgin IBA and reduced hazardous waste management costs provide an increased efficiency and cost-effective manufacturing operation.

For a manufacturing system 10 according to FIG. 1, manufacturing inputs 12 to the manufacturing process 14 include raw materials, labor, utilities, etc. In a manufacturing process, IBA can be an input to the process 14 as a raw material. The illustrated manufacturing process 14 produces partially or completely manufactured goods 16 and associated with such goods can be by-products. In a manufacturing process, one by-product can be a spent solvent 18 that can include IBA and hence can be disposed and treated as a hazardous waste; however, in a system 10 according to FIG. 1, the spent solvent 18 can be presented to an IBA Recovery Process 20 to recover usable IBA from the spent solvent 18 and return the recovered IBA 22 to the manufacturing process 14. One of ordinary skill in the art will recognize that the solvent can be understood to be a substance, including a liquid, in which another substance, including another liquid, is dissolved. As indicated herein, by returning recovered IBA 22 to the manufacturing process 14, the demand and hence cost for virgin IBA decreases, and the net amount of spent solvent 18 or hazardous waste (i.e., post IBA Recovery 20) also decreases to similarly reduce hazardous waste management costs.

Figure 2:
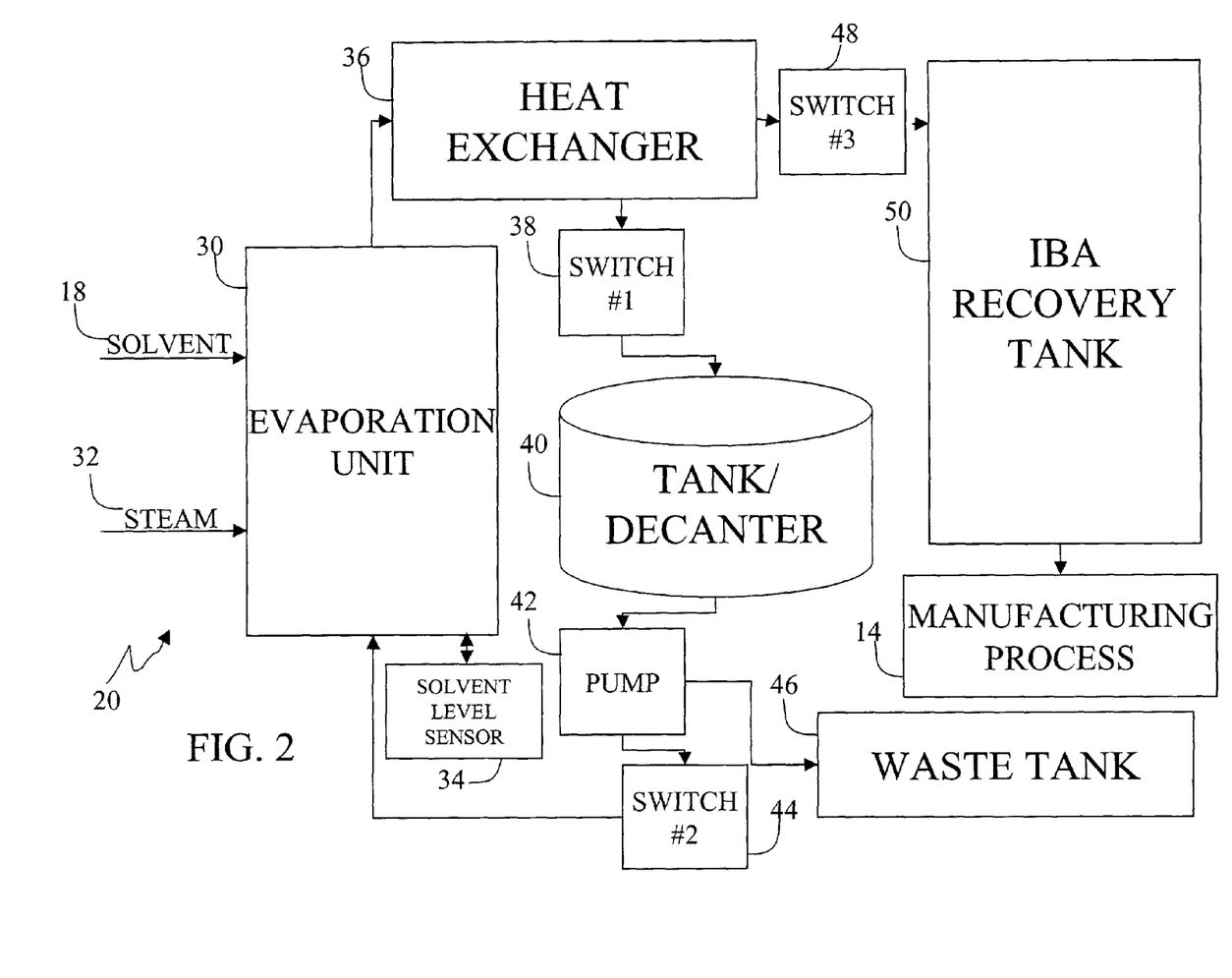
FIG. 2 illustrates one IBA recovery system for a IBA manufacturing process.

FIG. 2 provides an illustrative IBA Recovery Process 20. Per FIG. 2, the spent solvent 18 produced as a by-product from a manufacturing process 14 that can include, for example, a manufacturing process according to FIG. 1, is input to an Evaporation Unit 30 with steam 32. Those with ordinary skill in the art will recognize that the FIG. 2 IBA Recovery Process 20 provides an exemplary evaporation process, however, recovery can also occur using distillation or other methods, and the methods and systems herein are not limited to the recovery methodology or process.

In the illustrated system, the spent solvent 18 can be a liquid solution that includes water, IBA, and other production-related materials that can be stored in, for example, a holding tank. As the solvent 18 is transferred to the Evaporation Unit 30, the volume of the solution in the Unit 30 can be measured by a sensor 34 that can measure the solution level in the Evaporation Unit 30 and can be configured to provide an input to control when a heat source within the Evaporation Unit 30 can be applied to the solution in the Unit 30. Because the boiling temperature of IBA is greater than the boiling temperature of water, as the solution in the Unit 30 is heated, initially, material evaporating from the solution includes water and IBA. For a system according to FIG. 2, the evaporated material can enter a heat exchanger 36 that can cool the evaporated material to return the material to a liquid form. At this time, switch #1 38 is closed and switch #3 48 is open, and hence the liquid from the heat exchanger 36 returns to a tank 40 that also serves as a decanter. Because the density of IBA and water are different, the IBA and water can separate in the decanter tank 40, wherein a pump 42 operating in coordination with switch #2 44 can return IBA from the tank 40 to the evaporation unit 30, and water (and/or remaining solution) to a waste tank 46. Those with ordinary skill in the art will recognize that the process of transferring the IBA and water from the tank 40 to the evaporation unit 30 and waste tank 46 can be performed manually or automatically without departing from the scope of the disclosed methods and systems.

Because the separation of the water and IBA from the decanter tank 40 is not exact, the waste tank contents can include IBA and therefore the waste tank solution can be treated as hazardous waste; however, because of the iterative process of IBA recovery described above and continued herein, the solution in the waste tank 46 can be a fraction of the amount of solvent 18 entering the evaporation unit 30.

Meanwhile, the temperature in the Evaporation Unit 30 can continue to increase, where such temperature increases can be controlled manually or automatically, and can be controlled based on a linear and/or non-linear control As the temperature increases, increasing amounts of water evaporate and hence more IBA is returned to the Evaporation Unit 30 through switch #2 44, until the temperature in the Evaporation Unit 30 exceeds the boiling temperature of water. For a system according to FIG. 2, once the boiling temperature of water is exceeded in the Evaporation Unit 30, the Evaporation Unit temperature can be rapidly increased, linearly and/or non-linearly, to the boiling temperature of IBA. A control system can be implemented for a system according to FIG. 2 such that when the Evaporation Unit temperature approaches the evaporation temperature of IBA, switch #1 38 can open and switch #3 48 can close to cause the evaporated IBA to pass through the heat exchanger 36, convert to liquid form, and be stored in an IBA recovery tank 50. The IBA recovery tank contents can thereafter be used as an input to a manufacturing process 14, such as, for example, a process according to FIG. 1. Those with ordinary skill in the art will recognize that in some embodiments, the IBA recovery tank contents can be subjected to testing for quality before being utilized in the manufacturing process.

Those of ordinary skill in the art will recognize that the disclosed methods and systems can employ various embodiments with multiple variations. For example, in a continuous IBA recovery system according to FIG. 2, a recovery tank 50 may not be employed. This and/or other modifications can be made as are in the art, without departing from the scope of the disclosed methods and systems.

For an IBA manufacturing process 14 according to FIG. 1 that can implement an IBA recovery system such as that illustrated in FIG. 2, a dynamic performance measure (DPM) can be provided to maximize IBA recovery and steam use, and hence minimize hazardous waste cost and electricity cost. U.S. Pat. No. 5,134,574, to Beaverstock et al., entitled "Performance control apparatus and method in a processing plant," includes further detail on DPMs and is incorporated herein by reference in its entirety. DPMs are metrics that model performance measures in process manufacturing operations, wherein the metrics are derived from process instrumentation. DPMs can thus be calculated from a production process using real time, preferably object-based process data to display results in real-time to operations, engineering, management, maintenance, and/or appropriate manufacturing or other personnel, as decision support tools for real-time plant operations. In an embodiment, the DPMs can be presented graphically, and the DPM results can be historized into a real-time database management system for later use, aggrandizement, and integration with other computer information systems of the manufacturing plant.

DPMs for a particular plant operation can be based on a business strategy for that operation. The DPMs for one process or group thereof in one plant may not be appropriate for the same process of a similar but different plant. For example, if a manufacturing or process plant is production limited, primary measures can include yield or another production-based statistic; but, if a manufacturing or process plant is not production limited, primary measures can be resource-based. Developing DPMs therefore includes determining a business strategy, and translating that strategy to specific measurements that can assist in determining whether the strategy is successful, and this success can be measured on a process-by-process basis.

Once specific measures are determined, sensor information to make the measures can be determined. In many manufacturing and process plants, the sensors to make the measures are already installed in the manufacturing or control process. In some cases, new sensors can be installed to complete the collection of sensor-based information to measure the manufacturing or process operations.

The sensor measurements can be input to a computer or other processing module that includes a processor with instructions for causing the processor to act in accordance with the disclosed methods and systems. In an embodiment, the sensors can transmit a digital or analog signal to the processor that is equipped with appropriate input/output capability to receive the sensor-based information. The computer can convert, as necessary, the incoming sensor signals into digital values that can be formed into an input block that includes a collection of records or fields for sensor data. In an embodiment, a particular input block can correspond to a particular sensor. An input block can also provide general system access to the sensor data by name, where the global name is based on the name assigned to the input block. This data point or "object" value can be available to any application on the processor device or computer, or to other processor devices or computers in a network to which the processor device or computer is connected, by specifying the name of any input block or the name of the field or record of interest in the input block.

Calculation algorithms or mathematical relationships can also be formulated as part of the DPM construction. The calculation algorithms can mathematically relate the sensor measurements to a measure of the manufacturing performance. The calculation algorithms can also include targeted values, predetermined values, and comparisons between presently calculated values and the target values.

In an embodiment, an object-oriented programming based block structure can be established for a computation algorithm. These algorithm blocks can be preprogrammed for DPMs that are frequently encountered, or they can be programmed for different applications. The sensor-based data can be input to the algorithm blocks, and this can be accomplished by identifying in the algorithm block, an input block name and an input block parameter (field or record) of interest. The sensor data can therefore be input to the algorithm block and manipulated according to the mathematical relationships in the algorithm block.

The algorithm block output can be a global object that may be accessed by the computer or another computer in a network, for example, by specifying the name of the producing algorithm block. The output object values can be a basis for the DPMs of interest.

In an embodiment, in an algorithm block, the current overall performance of a manufacturing or plant operation, or process unit(s) of a plant, can be computed based on the sensor measurements. The calculated performance can be compared to a targeted performance measure as stored in, for example, an algorithm block or in a historian database. The comparison results can be presented to a display object and/or a historical database.

Display objects and display templates can be constructed for standard presentations of the DPMs, and can include line graphs that depict the DPM value over a period of time (historized), an indication of the DPM target value, and an indication of pertinent alarm limits. In an embodiment, the x and y axes can be labeled for the application and can include a directional indicator showing the direction of increasing performance. Display objects can be combined with other graphics to build an entire display template.

Subsequent to the building and displaying of the comparison results in various display objects, an operator/user can adjust controls and hence processes accordingly. The real-time display of the compared calculated performance and target performance in terms of production/resource factors of administration, can enable operator adjustment of processes, and hence resource/production factors, immediately during subject manufacturing toward target performance, i.e., toward desired values of resource/production factors. These adjustments can be recorded in a historian database. A historical database can therefore include sensed states of processes, operator adjustments, calculated performance measurements, and predefined target measures. Because an operator can receive real-time feedback of economic performance, adjustments to a process can be evaluated based on the adjustments' impact on performance.

Returning now to an IBA manufacturing and recovery processing system, such as those according to FIGS. 1 and 2, manufacturing strategies include producing an end product at a lowest possible cost. These manufacturing strategies thus include maximizing IBA recovery while minimizing costs that can be associated with virgin IBA demands, hazardous waste disposal, steam, and electricity. Accordingly, DPM calculation algorithms or mathematical relationships can be defined as follows:

$$\text{Value from Recovered IBA} = (\text{IBA flow to the recovery tank}) * (\text{cost per unit volume of virgin IBA}) \quad (1a)$$

$$\text{System Throughput} = (\text{IBA flow to the recovery tank}) \quad (1b)$$

As Equation (1a) indicates, the amount of savings from an IBA recovery process 20 such as those according to FIGS. 1 and 2 can be estimated by generating a DPM that includes the flow rate of the IBA into a recovery tank such as that provided in FIG. 2 50, and the purchase or market price of virgin IBA.

For the illustrated systems of FIGS. 1 and 2, a DPM can also be formed to represent the hazardous waste cost. Because hazardous waste disposition can be related to a cost per unit volume, a hazardous waste DPM can be generated according to Equation (2):

$$\text{Hazardous Waste Cost} = (\text{hazardous waste flow}) * (\text{disposition cost per unit volume}) \quad (2)$$

Additionally, for a system according to FIG. 2 where steam can be an input to the Evaporation Unit 30, a DPM can represent the cost of steam per unit IBA recovered to the process. In some systems, industrial boilers that can be located throughout a manufacturing plant can produce steam that can be input to a FIG. 2 Evaporation Unit 30. Additionally and optionally, boilers can generate steam that can be commonly utilized by different processes and/or manufacturing systems. Steam flow can be measured in units of lb/hr (pounds of steam per hour), wherein a DPM representing steam cost can be computed as represented by Equation (3):

$$\text{IBA Steam Cost} = \text{Steam flow} * \text{Steam generation cost} \quad (3)$$

For a system according to FIG. 2, IBA steam cost can be computed per unit time (e.g., hour), while steam flow can be measured in volume or weight (e.g., pounds or liters) per unit time by sensors that can include flow meters, orifice plates, etc., although such examples are provided for illustration and not limitation. Additionally, steam generation cost as indicated by Equation (3), can be indicated in cost per unit volume or weight, wherein steam generation cost can be related to costs of water, fuel costs to heat water that generates steam, etc.

Although Equation (3) includes a DPM representing the IBA steam cost to the Evaporation Unit, a IBA recovery steam cost can be computed based on the cost of steam per unit volume or weight of IBA recovered. Accordingly, a DPM can be constructed according to Equation (4):

$$\text{Steam cost per unit IBA recovered} = \text{IBA steam cost}/(\text{IBA flow to the recovery tank}) \quad (4)$$

Those with ordinary skill in the art will recognize that the units for the parameters in Equation (4) must be harmonized to provide a proper DPM. For example, IBA flow to the recovery tank can be measured in units of flow rate/hour, while IBA steam cost can be computed in cost/hour.

Additionally, a DPM can be constructed for IBA recovery systems that relates to electricity cost and/or usage. For example, Equation (5) represents one electricity cost DPM that can be computed:

$$\text{Electricity cost per unit IBA recovered} = (\text{Electricity cost per hour}) * (\text{IBA flow to the Recovery Tank}) \quad (5)$$

As with all of the DPMs, proper integration of measurements can be utilized to achieve the desired objective. For example, electrical consumption can be measured in kilowatts, while electricity cost can be measured in dollars per kilowatt-hour, to provide a DPM in cost per hour, although such an example is provided for illustration and not limitation.

Those with ordinary skill in the art will recognize that the measurements for the DPMs as indicated by Equations (1) through (5) can be derived according to sensors designed to measure flow rates, for example, including flow meters that can measure the flows to the waste tank 46 and the IBA recovery tank 50. One flow meter can include a common orifice plate and differential transmitter combination. Another alternative is a vortex flow meter, and those with ordinary skill in the art will recognize that other measurement sensors can provide the flow rate according to the methods and systems herein. According to the DPMs, such flow rates can be measured in real-time.

Figure 3:
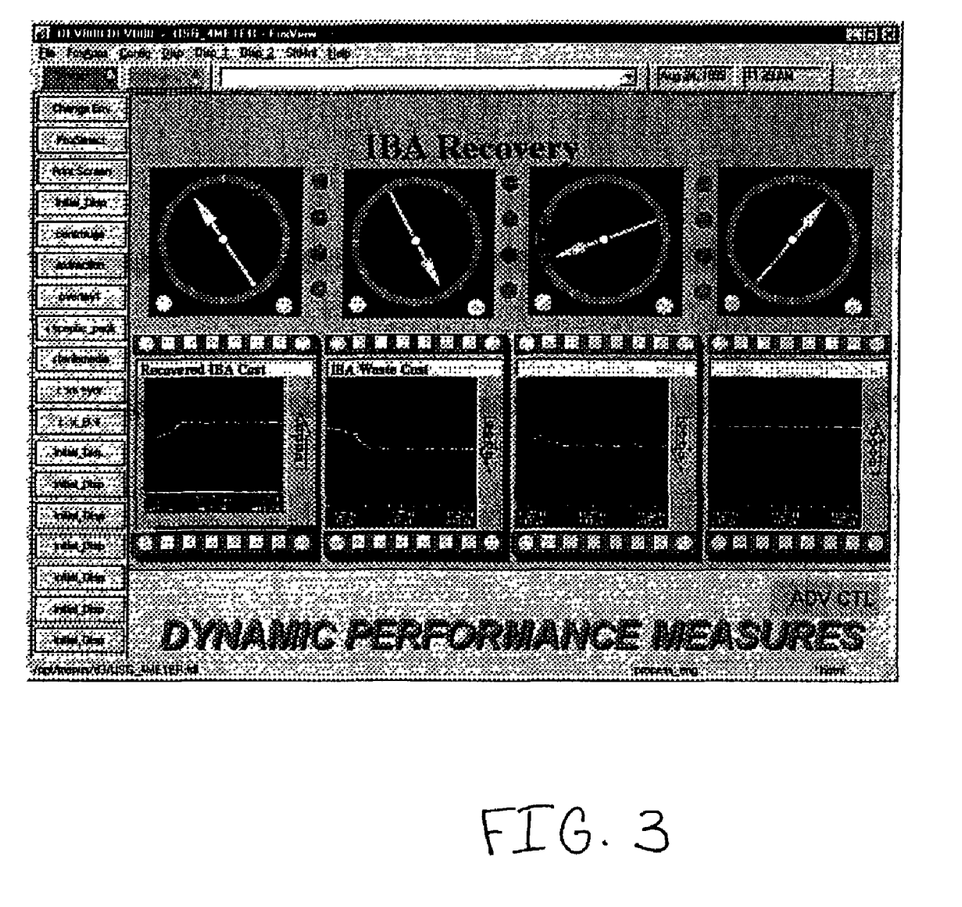
FIG. 3 shows exemplary Dynamic Performance Measures (DPMs) for an IBA manufacturing process.

In an embodiment, for example, an engineer or another viewing the FIG. 3 DPMs can determine that the recovered IBA is decreasing while the volume of waste material is increasing in real-time. Such a determination may indicate that the temperature of the evaporation unit 30 may not be properly controlled, which may indicate a problem with either the temperature sensor or the temperature control unit. Alternately, the operation of the pump may be at issue. These issues are presented merely for illustration and not limitation.

Figure 4:
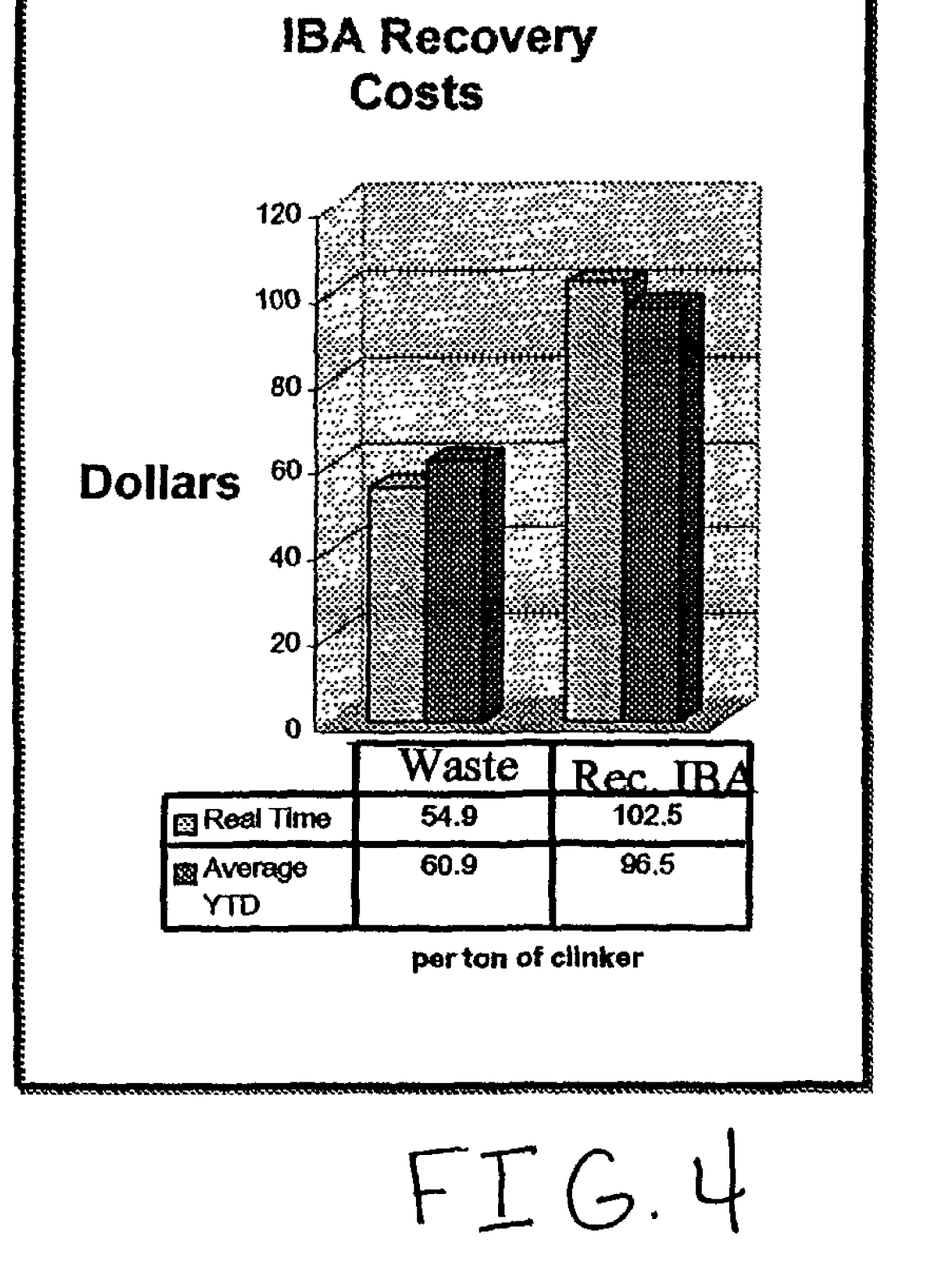
FIG. 4 is an example management display that can be generated from historized data of DPMs such as those of FIG. 3; and, FIG. 5 illustrates one embodiment of an I/A Series system.

FIG. 3 provides a display of the DPMs for indicating the cost reductions for recovered IBA and the costs of hazardous waste disposal as a function of real-time. An engineer, operator, manufacturing personnel, etc. can view the displays and make manufacturing decisions in real-time to affect the manufacturing costs. FIG. 4 presents an alternate display that can be utilized for reports and can be created from historized data to indicate the effectiveness of the manufacturing strategy.

Those with ordinary skill in the art will recognize that although FIGS. 3 and 4 were presented in the illustrated display formats, the methods and systems herein are neither limited to the information displayed, nor the format of the displayed information. Although FIGS. 3 and 4 do not provide DPM displays for the steam and electricity DPMs of Equations (3), (4), and (5), those with ordinary skill in the art will recognize that DPM displays similar to those presented in FIGS. 3 and 4 can be presented for the steam and electricity DPMs of Equations (3), (4), and (5).

Figure 5:
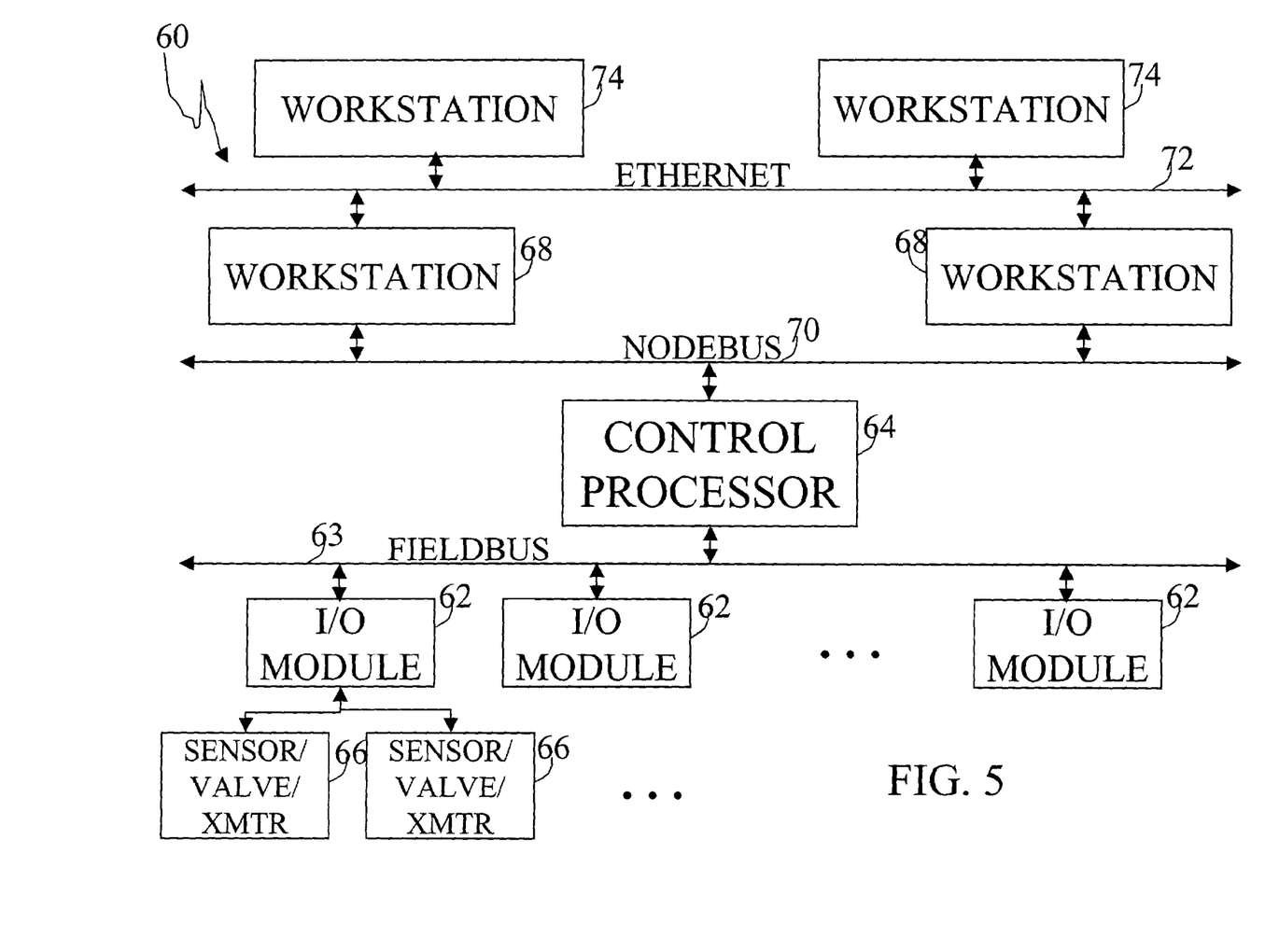

FIG. 5 presents an illustrative system 60 that can be implemented in a IBA recovery manufacturing process such as the system of FIGS. 1 and 2, and can further provide for implementation of DPMs as provided herein, and is known as the I/A Series® system from Invensys Systems, Inc. As is well-known, the I/A Series® system includes I/O Modules 62 such as the FBM44 modules, wherein the I/O Modules 62 can interface to a Fieldbus 63 and hence to a Control Processor 64 such as the I/A Series® CP40B. Data from sensors 66 can be transferred to the I/O modules 62 using a transmitter, wherein the I/O Modules 62 can convert the sensor data to a format compatible with the Control Processor 64. In one embodiment of the system, the Control Processor 64 can include at least one processor that includes instructions for causing the processor to implement control algorithms. The Control Processor 64 can further include instructions for implementing DPMs such as those provided herein by Equations (1) and (2). As shown for the FIG. 4 system, the Control Processor 64 can interface to Workstations 68 through an I/A Series Nodebus 70 that can be compatible with Ethernet. The Workstations can be, for example, the I/A Series system AW51E that or another system. The Workstations 68 can have access to one or more internal or external databases, and can allow for the display of data such as data based on FIGS. 3 and 4 herein, to allow a processor engineer, manufacturing personnel, etc., to monitor and/or affect the controlled systems. The illustrated Workstations 68 can further interface to another Ethernet 72 that provides an interface to, for example, a corporate network that can be equipped with other Workstations 74, Personal Computers (PCs), etc., that can also have instructions for causing the display of DPM and/or other information to management or other entities. Historic information can also be provided to such systems 74 for local retrieval and analysis.

Returning to the Control Processor 64 of FIG. 5, depending upon the control algorithms, DPM computations, and any integration therein, the Control Processor 64 can be equipped to transfer control data to, for example, the valves or sensors 66 via the I/O Modules 62 to achieve specified control objectives. In one embodiment, the control objectives can be pre-programmed using a multivariable control system such as the Connisseur system provided by Invensys Systems, Inc., however in other embodiments, manufacturing or other process system adjustments can be made manually or through the I/A Series Workstations 68.

As indicated earlier, alarms can be utilized to indicate to manufacturing personnel in real-time that certain, predefined limits are being exceeded or otherwise satisfied.

What has thus been described are methods and systems for creating dynamic performance measures (DPMs) for an IBA manufacturing process. In an embodiment, IBA recovery and waste material production can be optimized by aggregating sensor measurements from sensors that produce outputs indicating the amounts of IBA recovered and waste material generated, respectively. The respective sensor measurements can be processed to form a measurement that can be utilized to determine measures in the form of DPMs that relate to the productivity and cost of the IBA recovery and waste management processes. The DPMs can be provided to a display that can be viewed by manufacturing or other personnel. Control decisions can be made to change the IBA recovery and/or waste production processes while the results of such changes can be reflected in real-time on the DPM displays.

Although the methods and systems have been described relative to a specific embodiment thereof, they are not so limited. Obviously many modifications and variations may become apparent in light of the above teachings. For example, any sensors providing the necessary sensor measurements can be used to construct the desired DPMs. The DPMs can be displayed using any type of graphical user interface (GUI) that is suitable for presenting information according to the application of interest.

The methods and systems described herein are not limited to a particular hardware or software configuration, and may find applicability in many computing or processing environments. The methods and systems can be implemented in hardware or software, or a combination of hardware and software. The methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) is preferably implemented using one or more high level procedural or object-oriented programming languages to communicate with a computer system; however, the program(s) can be implemented in assembly or machine language, if desired. The language can be compiled or interpreted.

The processor(s) can thus be embedded in one or more devices that can be operated independently or together in a networked environment, where the network can include, for example, a Local Area Network (LAN), wide area network (WAN), and/or can include an intranet and/or the internet and/or another network. The network(s) can be wired or wireless or a combination thereof and can use one or more communications protocols to facilitate communications between the different processors. The processors can be configured for distributed processing and can utilize, in some embodiments, a client-server model as needed. Accordingly, the methods and systems can utilize multiple processors and/or processor devices, and the processor instructions can be divided amongst such single or multiple processor/devices.

The device(s) or computer systems that integrate with the processor(s) can include, for example, a personal computer (s), workstation (e.g., Sun, HP), personal digital assistant (PDA), handheld device such as cellular telephone, or another device capable of being integrated with a processor(s) that can operate as provided herein. Accordingly, the devices provided herein are not exhaustive and are provided for illustration and not limitation.

Many additional changes in the details, materials, and arrangement of parts, herein described and illustrated, can be made by those skilled in the art. Accordingly, it will be understood that the following claims are not to be limited to the embodiments disclosed herein, can include practices otherwise than specifically described, and are to be interpreted as broadly as allowed under the law.

What is claimed is:

1. A method for monitoring an Isobutyl Alcohol (IBA) recovery system during system operation, comprising,
    a) determining, by using at least one sensor, at least one of an amount of IBA recovered from the IBA recovery system and an amount of waste material produced from the IBA recovery system during system operation,
    b) computing, by using at least one processor operatively coupled to said at least one sensor, at least one of: a cost of IBA saved as a result of the amount of IBA recovered during system operation, a cost of waste material management as a result of the amount of waste material produced from the IBA recovery system during system operation, an IBA recovery system electricity cost for electricity used during system operation, and an IBA recovery system steam cost for steam used during system operation,
    c) displaying to at least one user by way of at least one output device operatively coupled to said at least one processor at least one of the said costs, the amount of recovered IBA and the amount of waste material produced based on a measuring time during system operation;
    d) in response to input based upon at least one of the said displayed costs and amounts, which input is received by means of at least one input device from said at least one user, making at least one change to at least one process of the recovery system; and
    e) repeating steps a) to d) until a reduction in at least one of the said costs during system operation is achieved.

2. A method according to claim 1, wherein determining an amount of waste material produced comprises,
    measuring waste material flow.

3. A method according to claim 1, further comprising measuring at least one of a flow rate of recovered IBA and a flow rate of waste material.

4. A method according to claim 1, wherein the IBA recovery system includes at least one of an evaporation IBA recovery system and a distillation IBA recovery system.

5. A method according to claim 1, wherein determining the amount of IBA recovered from the IBA recovery system includes determining an amount of IBA recovered per unit volume.

6. A method according to claim 1, further comprising providing an alarm when the amount of IBA recovered satisfies at least one criterion.

7. A method according to claim 1, further comprising providing an alarm when the amount of waste material produced satisfies at least one criterion.

8. A method according to claim 1, further comprising,
    determining a cost of steam provided to the IBA recovery system, and
    computing a steam cost per unit of IBA recovered based on the flow rate of recovered IBA and the measured cost of steam.

9. A method according to claim 1, further comprising,
    measuring electrical consumption related to the IBA recovery system, and,
    computing a measure of IBA recovery system electricity cost based on the measured electrical consumption and a cost of electricity.

10. A method according to claim 1, further comprising,
    measuring a flow of steam to the IBA recovery system, and,
    computing a measure of IBA recovery system steam cost based on the flow of steam and a cost of steam generation.

* * * * *